United States Patent
Lefebvre et al.

(10) Patent No.: US 9,434,203 B2
(45) Date of Patent: Sep. 6, 2016

(54) SECURITY ELEMENTS EXHIBITING A DYNAMIC VISUAL MOTION

(71) Applicant: SICPA HOLDING SA, Prilly (CH)

(72) Inventors: Olivier Lefebvre, Montagny-pres-Yverdon (CH); Catherine Fankhauser, Chavannes-de-Bogis (CH)

(73) Assignee: SICPA HOLDING SA, Prilly (CH)

( * ) Notice: Subject to any disclaimer, the term of this patent is extended or adjusted under 35 U.S.C. 154(b) by 0 days.

(21) Appl. No.: 14/888,273

(22) PCT Filed: Apr. 15, 2014

(86) PCT No.: PCT/EP2014/057569
§ 371 (c)(1),
(2) Date: Oct. 30, 2015

(87) PCT Pub. No.: WO2014/177375
PCT Pub. Date: Nov. 6, 2014

(65) Prior Publication Data
US 2016/0075162 A1 Mar. 17, 2016

(30) Foreign Application Priority Data
May 1, 2013 (EP) .................................... 13166117

(51) Int. Cl.
*G01N 21/64* (2006.01)
*G07D 7/12* (2016.01)
(Continued)

(52) U.S. Cl.
CPC .............. *B42D 25/29* (2014.10); *B41F 11/02* (2013.01); *B42D 25/405* (2014.10); *G01N 21/64* (2013.01);
(Continued)

(58) Field of Classification Search
CPC ...... B41F 11/02; B42M 3/144; B42M 3/148; B24D 25/29; B24D 25/405; G01N 21/64; G01N 2201/062; G07D 7/128
See application file for complete search history.

(56) References Cited

U.S. PATENT DOCUMENTS

| 5,211,877 A | 5/1993 | Andrejewski et al. |
| 5,362,315 A | 11/1994 | Muller-Rees et al. |

(Continued)

FOREIGN PATENT DOCUMENTS

| DE | 10211310 | 10/2003 |
| EP | 0601483 | 6/1994 |

(Continued)

OTHER PUBLICATIONS

"The Printing Ink Manual", 5th Edition, ed. Leach et al., (2008), pp. 58-62.
(Continued)

*Primary Examiner* — Mark R Gaworecki
(74) *Attorney, Agent, or Firm* — Greenblum & Bernstein, P.L.C.

(57) ABSTRACT

The present invention is related to a security element comprising a pattern of at least three layers, wherein a first layer comprises a first material which is capable of interacting with a first electromagnetic radiation but does not interact with a second and third electromagnetic radiation, a second layer comprises a second material which is capable of interacting with said second electromagnetic radiation but does not interact with a first and third electromagnetic radiation, and a third layer comprising a third material which is capable of interacting with a third electromagnetic radiation but does not interact with a first and second electromagnetic radiation, wherein said pattern provides a visual motion effect when exposed to a sequential illumination with a light source capable of separately emitting at least said first, second and third electromagnetic radiation. The present invention is furthermore related to the security element, the use of the security element for the protection of a security document against fraud or illegal reproduction, to a method for manufacturing the security element or security document, and to a method for creating a visual motion effect by sequential illumination of the security element.

15 Claims, 3 Drawing Sheets

(51) Int. Cl.
*B42D 25/29* (2014.01)
*B42D 25/40* (2014.01)
*B42D 25/405* (2014.01)
*B41F 11/02* (2006.01)
*B41M 3/14* (2006.01)

(52) U.S. Cl.
CPC .............. *G07D 7/128* (2013.01); *B41M 3/144* (2013.01); *B41M 3/148* (2013.01); *B42D 2033/26* (2013.01); *B42D 2035/34* (2013.01); *G01N 2201/062* (2013.01)

(56) References Cited

U.S. PATENT DOCUMENTS

| | | |
|---|---|---|
| 6,410,130 B1 | 6/2002 | Schuhmacher et al. |
| 6,423,246 B1 | 7/2002 | Kasch et al. |
| 6,565,770 B1 | 5/2003 | Mayer et al. |
| 7,517,578 B2 | 4/2009 | Raksha et al. |
| 2007/0037290 A1 | 2/2007 | Hoshino et al. |
| 2008/0054621 A1 | 3/2008 | Burchard et al. |
| 2012/0074682 A1 | 3/2012 | Rosset |
| 2012/0174447 A1 | 7/2012 | Vincent |
| 2012/0308072 A1 | 12/2012 | Lefebvre et al. |

FOREIGN PATENT DOCUMENTS

| | | |
|---|---|---|
| EP | 1046692 | 10/2000 |
| EP | 1213338 | 6/2002 |
| EP | 1684098 | 7/2006 |
| EP | 2529940 | 12/2012 |
| WO | 03/077193 | 9/2003 |
| WO | 2004/007095 | 1/2004 |
| WO | 2008/033059 | 3/2008 |
| WO | 2008/092522 | 8/2008 |
| WO | 2009/005733 | 1/2009 |
| WO | 2011/092502 | 8/2011 |
| WO | 2012/104098 | 8/2012 |

OTHER PUBLICATIONS

"Printing Technology", Delmar Thomson Learning, 5th Edition, ed. Adams et al., (2002), pp. 293-328, 302-312, 359-360.

Kipphan, "Handbook of Print Media", Springer, (2001), pp. 48.

Fig. 1B  Fig. 1C  Fig. 1D

Fig. 5A   Fig. 5B   Fig. 5C
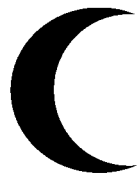 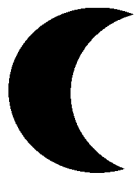 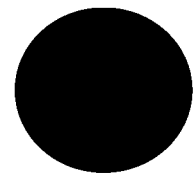
Fig. 5D   Fig. 5E   Fig. 5F
 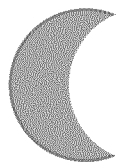 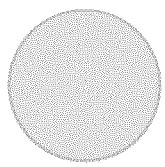
Fig. 5G
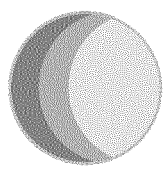

SECURITY ELEMENTS EXHIBITING A DYNAMIC VISUAL MOTION

FIELD OF THE INVENTION

The present invention relates to the field of security elements and their uses for the protection of security documents against counterfeit and illegal reproduction. In particular, the present invention relates to the field security elements displaying a dynamic visual motion when exposed to a sequential illumination.

BACKGROUND OF THE INVENTION

With the constantly improving quality of color photocopies and printings and in an attempt to protect security documents such as banknotes, value documents or cards, transportation tickets or cards, tax banderols, and product labels that have no reproducible effects against counterfeiting, falsifying or illegal reproduction, it has been the conventional practice to incorporate various security means in these documents. Typical examples of security means include security threads, windows, fibers, planchettes, foils, decals, holograms, watermarks, security inks comprising optically variable pigments, magnetic or magnetizable thin-film interference pigments, interference-coated particles, thermochromic pigments, photochromic pigments, luminescent, infrared-absorbing, ultraviolet-absorbing or magnetic compounds.

In addition to static security features used for protecting security documents against counterfeit and illegal reproduction, dynamic security features providing the optical illusion of movement have been developed. In particular, security elements based on oriented magnetic or magnetizable pigments and magnetic or magnetizable optically variable pigments have been developed so as to provide an optical illusion of movement.

WO 2004/007095 A2 discloses the creation of a dynamic optically variable effect known as the "rolling-bar" feature. The "rolling-bar" feature provides the optical illusion of movement to images comprised of oriented magnetic or magnetizable pigments. A printed "rolling bar" type image shows a contrasting band which appears to move ("roll") as the image is tilted. U.S. Pat. No. 7,517,578 and WO 2012/104098 A1 respectively disclose "double rolling bar" and "triple rolling bar" features, said features seeming to move against each other upon tilting.

WO 2011/092502 A2 discloses moving-ring images displaying an apparently moving ring with changing viewing angle ("rolling ring" effect), said moving-ring images being comprised of oriented magnetic or magnetizable pigments.

Alternatively, methods have been developed to provide security elements displaying a real dynamic motion. US 2012/0074682 discloses a method for creating a visual animation on a medium, the disclosed method include a step of disposing at least two excitable agents on the medium in at least two adjacent respective zones, each of said agents generating a visual effect in response to one and the same stimulus. US 2012/0174447 discloses a security element comprising an optical system that may exhibit a visual animation effect during successive observations by changing the direction of observation of the security element. The disclosed optical system comprises a transparent or translucent substrate, on the side of a first surface of the substrate a combined image comprising a plurality of encoded interleaved images, on the side of second surface of the substrate opposite the first, an exposing screen placed on top of the combined image, which enables the encoded images to be observed during a change in the direction of observing the security element relative to the optical system, wherein the encoded images are observable from the side of the first surface and from the side of the second surface of the substrate.

A need remains for security elements displaying a dynamic visual motion as anti-copy protection means for security documents, said security elements combining an easy detection and recognition while still being difficult to copy.

SUMMARY OF THE INVENTION

Accordingly, it is an object of the present invention to provide security elements and security documents comprising said security elements displaying a dynamic visual motion when exposed to a sequential illumination. This is achieved by the security element of claim 1. In particular, the present invention is related to a security element comprising a pattern of at least three layers, wherein a first layer comprises a first material which is capable of interacting with a first electromagnetic radiation but does not interact with a second and third electromagnetic radiation, a second layer comprises a second material which is capable of interacting with said second electromagnetic radiation but does not interact with a first and third electromagnetic radiation, and a third layer comprising a third material which is capable of interacting with a third electromagnetic radiation but does not interact with a first and second electromagnetic radiation, wherein said pattern provides a visual motion effect when exposed to a sequential illumination with a light source capable of separately emitting at least said first, second and third electromagnetic radiation.

Also claimed and described herein are uses of the security elements described for the protection of a security document against fraud or illegal reproduction as well as security documents comprising the security elements described herein.

Also claimed and described herein are processes for manufacturing said security element, comprising a step of applying, preferably by a coating or printing process, at least a first ink composition comprising said first material so as to form said first layer, and applying, preferably by a coating or printing process, at least a second ink composition comprising said second material so as to form said second layer, and applying, preferably by a coating or printing process, a third ink composition comprising said third material so as to form said third layer so as to form a pattern providing a visual motion effect when exposed to a sequential illumination with a light source capable of separately emitting said first, second and third electromagnetic radiation.

Also claimed and described herein are methods for creating a visual motion effect, comprising the steps of providing said security element, and sequentially illuminating said security element with a light source capable of separately emitting at least said first, second and third electromagnetic radiation.

The sequential illumination of the first, second and third layers of the pattern described herein allows an observer to see a visual motion. The sequential illumination may reveal a succession of the layers by using a light source, thereby making the security element possible to create a visual motion visible to an observer. The dynamic nature of the security elements described herein upon exposure to a sequential illumination cannot be captured by photocopying said security elements as such their security level is particularly high.

BRIEF DESCRIPTION OF DRAWINGS

FIGS. 1A-1E represent an embodiment of the security element of the present invention which under sequential illumination exhibits a visual motion of a wheel. FIG. 1A is a side view of said security element. FIG. 1B is a top view of layer 1 of the security element of FIG. 1A providing a first position of said wheel. FIG. 1C is a top view of layer 2 of the security element of FIG. 1A providing a second position of said wheel. FIG. 1D is a top view of layer 3 of the security element of FIG. 1A providing a third position of said wheel. FIG. 1E is a top view of the security element of FIG. 1 A showing the superimposition of layers 1 to 3.

FIGS. 2A-2C are top views of superimposed layers of said security element providing different positions of said spiral.

FIGS. 3A-3C are top views of superimposed layers of said security element providing different positions of said horse-drawn carriage.

FIGS. 4A-4C are top views of spaced-apart layers of said security element providing different positions of said ball.

FIGS. 5A-5C represent another embodiment of the security element of the present invention which under sequential illumination exhibits a visual motion of a waxing or waning moon. FIGS. 5A-5C are top views of spaced-apart layers of said security element providing different positions of said moon.

FIGS. 5D-5G represent another embodiment of the security element of the present invention which under sequential illumination exhibits a visual motion of a waxing or waning moon. FIGS. 5D-5F are top views of superimposed layers of said security element providing different positions of said moon. FIG. 5G is a top view of said security element of showing the superimposition of the layers shown in FIGS. 5D-5F.

DETAILED DESCRIPTION

Definitions

Figure 1A:
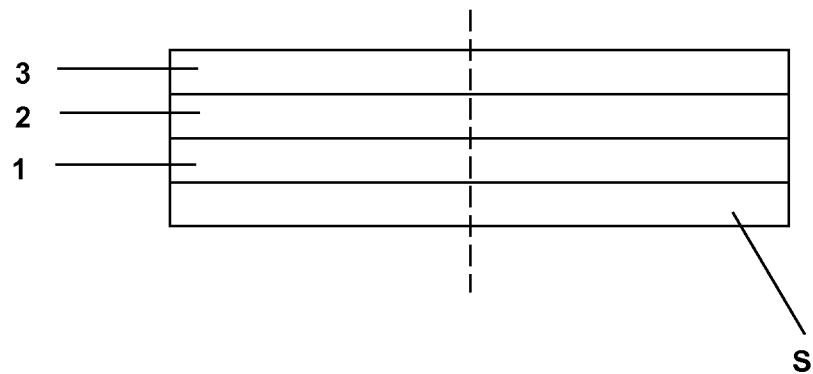
Figure 1A:
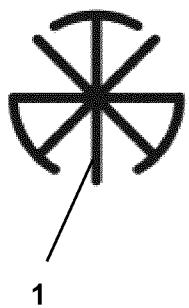
Figure 1A:
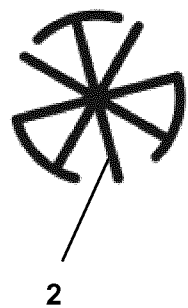
Figure 1A:
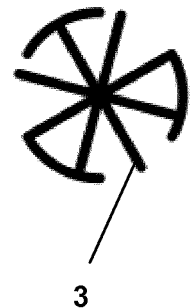

The following definitions are to be used to interpret the meaning of the terms discussed in the description and recited in the claims.

As used herein, the article "a" indicates one as well as more than one and does not necessarily limit its referent noun to the singular.

As used herein, the term "about" means that the amount or value in question may be the specific value designated or some other value in its neighborhood. Generally, the term "about" denoting a certain value is intended to denote a range within ±5% of the value. As one example, the phrase "about 100" denotes a range of 100±5, i.e. the range from 95 to 105. Preferably, the range denoted by the term "about" denotes a range within ±3% of the value, more preferably ±1%. Generally, when the term "about" is used, it can be expected that similar results or effects according to the invention can be obtained within a range of ±5% of the indicated value.

As used herein, the term "and/or" means that either all or only one of the elements of said group may be present. For example, "A and/or B" shall mean "only A, or only B, or both A and B". In the case of "only A", the term also covers the possibility that B is absent, i.e. "only A, but not B".

As used herein, the term "at least" is meant to define one or more than one, for example one or two or three.

The term "comprising" as used herein is intended to be non-exclusive and open-ended. Thus, for instance a composition comprising a compound A may include other compounds besides A.

The term "security element" shall designate an element or a feature on a security document for the purpose of determining its authenticity and protecting it against counterfeits and illegal reproduction.

The term "security document" refers to a document which is usually protected against counterfeit or fraud by at least one security feature. Examples of security documents include without limitation value documents and value commercial goods. Typical example of value documents include without limitation banknotes, deeds, tickets, checks, vouchers, fiscal stamps and tax labels, agreements and the like, identity documents such as passports, identity cards, visas, bank cards, credit cards, transactions cards, access documents, entrance tickets and the like.

The term "similar body" refers to different positions of one specific body in movement or in another form of alteration (such as a waxing and waning moon).

The term "visual motion" refers to an effect which is observed by the human eye as a movement or other alteration of a body (such as a waxing and waning moon).

The term "sequential illumination" refers to an illumination of the security element of the present invention with different kinds of electromagnetic radiation in a sequential manner, i.e. the security element is illuminated with a first electromagnetic radiation, followed by illumination with a second electromagnetic radiation, etc.

The term "adjacent" means a position of different layers of the security element of the present invention such that they are in contact with each other.

In one aspect, the present invention relates to a security element made of a pattern comprising at least three layers, i.e. at least a first layer, a second layer and a third layer, said security element might be disposed on a security document. The pattern comprising three or more layers described herein is produced by applying, preferably by a coating or printing process, at least three ink compositions so as to form at least three layers. According to a preferred embodiment, the at least three layers each correspond to a position of a similar body or of a similar graphical object composed of the at least three layers. The dynamic motion of the security element described herein is observable when an observer uses an appropriate illuminating equipment so as to create an impression of visual motion by providing a sequential visualization of the layers thus creating an impression of visual motion. According to a preferred embodiment of the present invention, the at least three layers represent a succession of at least three different positions of a similar body and represent as a security element a graphical object exhibiting, when exposed to a sequential illumination, a dynamic visual motion. In other words, upon exposure to a sequential illumination, the combination of the at least three layers corresponds to at least three different positions of a similar body thus providing to an observer the optical illusion of said body in motion.

The security element described herein comprises a first layer containing a first material which is capable of interacting with a first electromagnetic radiation but does not interact with a second and third electromagnetic radiation, a second layer containing a second material which is capable of interacting with said second electromagnetic radiation but does not interact with a first and third electromagnetic radiation, and a third layer containing a third material which is capable of interacting with a third electromagnetic radiation but does not interact with a first and second electromagnetic radiation. The security element can be manufactured by a process comprising a step of applying, preferably by a coating or printing process, at least a first ink composition comprising said first material so as to form said first layer, and applying, preferably by a coating or printing process, at least a second ink composition comprising said second material so as to form said second layer, and applying, preferably by a coating or printing process, a third ink composition comprising said third material so as to form said third layer so as to form a pattern providing a visual motion effect when exposed to a sequential illumination with a light source capable of separately emitting said first, second and third electromagnetic radiation.

Materials specifically interacting with one kind of electromagnetic radiation are known to a skilled man. For example, materials are known which only emit radiation when irradiated with e.g. UV- or IR radiation. Also, materials are known which only interact with circularly polarized light (chiral materials). According to the present invention, it is principally possible to use any of those materials in the security element of the present invention. Preferably, the first material described herein is selected from the group consisting of one or more left-handed circularly polarizing cholesteric liquid crystal materials. Preferably, the second material described herein is selected from the group consisting of one or more right-handed circularly polarizing cholesteric liquid crystal materials. Preferably, the third material described herein is selected from the group consisting of one or more luminescent materials.

According to a preferred embodiment of the present invention, the security element described herein comprises a) a first layer comprising one or more left-handed circularly polarizing cholesteric liquid crystal materials, b) a second layer comprising one or more right-handed circularly polarizing cholesteric liquid crystal materials and c) a third layer comprising one or more luminescent materials.

Liquid crystals in the cholesteric phase exhibit a molecular order in the form of a helical superstructure perpendicular to the longitudinal axes of its molecules. Cholesteric liquid crystal polymers can be obtained by subjecting one or more crosslinkable substances (nematic compounds) with a chiral phase to alignment and orientation. The particular situation of the helical molecular arrangement leads to cholesteric liquid crystal materials exhibiting the property of reflecting a circularly polarized light component within a determined wavelength range, i.e. cholesteric liquid crystal materials may be left-handed circularly polarizing cholesteric liquid crystal materials or right-handed circularly polarizing cholesteric liquid crystal materials. The pitch (i.e. the distance over which a full rotation of 360° of the helical arrangement is completed) can be tuned in particular by varying selectable factors including the temperature and solvents concentration, by changing the nature of the chiral component(s) and the ratio of nematic and chiral compounds. Crosslinking under the influence of UV radiation freezes the pitch in a predetermined state by fixing the desired helical form so that the properties of the resulting cholesteric liquid crystal materials are no longer depending on external factors such as the temperature. Preferably, the one or more cholesteric liquid crystal materials used in the present invention are cholesteric liquid crystal pigments. Cholesteric liquid crystal pigments can be incorporated in conventional ink compositions according to the printing method selected to print security elements described herein. Examples of suitable ink compositions may be found e.g. in The Printing Ink Manual, Ed R. H. Leach, R. J. Pierce, $5^{th}$ Edition. Cholesteric liquid crystal polymers may be shaped to cholesteric liquid crystal pigments by subsequently comminuting the polymer to the desired particle size. Examples of films and pigments made from cholesteric liquid crystal materials and their preparation are disclosed in U.S. Pat. Nos. 5,211,877; 5,362,315 and 6,423,246 and in EP 1 213 338 B1; EP 1 046 692 B1 and EP 0 601 483 B1, the respective disclosure of which is incorporated by reference herein. Suitable left- or right-handed circularly polarizing cholesteric liquid crystals pigments for the present invention are known in the art and have been disclosed e.g. in U.S. Pat. No. 6,410,130, EP 1 213 338 A1, EP 1 046 692 A1 or EP 0 601 483 A1, the respective disclosure of which is incorporated by reference herein.

Advantageously, cholesteric liquid crystal materials, due to their helical superstructure being at the origin of a periodic refractive index modulation throughout the liquid crystal material thus resulting in a selective transmission/reflection of determined wavelengths of light (interference filter effect), exhibit colorshifting properties (also referred in the art as optically variable or goniochromatic properties), i.e. they exhibit a viewing-angle or incidence-angle dependent color. Security elements exhibiting colorshifting properties are used to protect banknotes and other security documents against counterfeiting and/or illegal reproduction by commonly available color scanning, printing and copying office equipment so that the man on the street can easily check the authenticity of the security element by tilting said security element. In addition to the overt security provided by the colorshifting property of cholesteric liquid crystal materials, which allows easily detecting, recognizing and/or discriminating of security elements or security documents comprising said security element from their possible counterfeits with the unaided human senses, the colorshifting property of the cholesteric liquid crystal materials may be used as a machine readable tool for the recognition of security elements. Thus, the colorshifting properties of cholesteric liquid crystal materials may simultaneously be used as a covert or semi-covert security element in an authentication process wherein the optical (e.g. spectral) properties of the materials are analyzed. As mentioned above, optical characteristics of cholesteric liquid crystal materials include an interference effect. To generate or reveal color interference effect and strong colorshifting properties, the cholesteric liquid crystal materials described herein are preferably present directly or indirectly on an absorbing surface or to a background, preferably a sufficiently dark and even preferably a black surface or background. The term "absorbing surface" refers to a layer that absorbs at least part of the visible spectrum of light, preferably to a surface of a dark color, most preferably to a black surface.

Luminescent materials are widely used as marking materials in security applications. Luminescent compounds may be inorganic (inorganic host crystals or glasses doped with luminescent ions), organic or organometallic (complexes of luminescent ion(s) with organic ligand(s)) substances.

Luminescent compounds can absorb certain types of energy acting upon them and subsequently emit at least partially this absorbed energy as electromagnetic radiation. Luminescent compounds are detected by exposing them with a certain wavelength of light and analyzing the emitted light. Down-converting luminescent compounds absorb electromagnetic radiation at a higher frequency (shorter wavelength) and at least partially re-emit it at a lower frequency (longer wavelength). Up-converting luminescent compounds absorb electromagnetic radiation at a lower frequency and at least partially re-emit part of it at a higher frequency. Both fluorescent and phosphorescent compounds are suitable for the realization of the images comprised in the security element described herein. Luminescent dyes for the present invention are known in the art and may be selected from the group consisting of naphthalmides, coumarins, rhodamines, flurorescein, distyryl biphenyls, stilbenes, cyanines, phthalocyanines, xanthenes, thioxanthenes, naphtholactames, azlactones, methanes, oxazines, pyrazolines, polypyridyl-ruthenium complexes, polypyridyl-phenazine-ruthenium complexes, platinum-porphyrin complexes, long-life europium and terbium complexes and mixtures thereof. Typical examples of dyes suitable for the present invention are e.g. Solvent Yellow 44, Solvent Yellow 94, Solvent Yellow 160, Basic Yellow 40, Basic Red 1, Basic Violet 10, Acid Red 52, Yellow s790, fluorescein isothiocyanate, tris (2,2'-bipyridyl)-ruthenium chloride, tris(1,10-phenanthroline)-ruthenium chloride, octaethyl-platinum-porphyrin. Luminescent materials in pigment form have been widely used in inks (see U.S. Pat. No. 6,565,770, WO 2008/033059 A2 and WO 2008/092522 A1). Examples of luminescent materials include among others sulfides, oxysulfides, phosphates, vanadates, etc. of non-luminescent cations, doped with at least one luminescent cation chosen from the group consisting of transition-metal and the rare-earth ions; rare earth oxysulfides and rare-earth metal complexes such as those described in WO 2009/005733 A2 or in U.S. Pat. No. 7,108,742. Examples of inorganic materials include without limitation $La_2O_2S:Eu$, $ZnSiO_4:Mn$, and $YVO_4:Nd$. Luminescent materials can be incorporated in conventional ink compositions according to the printing method selected to print security elements described herein. Examples of suitable ink compositions may be found e.g. in The Printing Ink Manual, Ed R. H. Leach, R. J. Pierce, 5th Edition.

The security elements described herein are made of a pattern comprising at least three layers so as to produce a visual motion during sequential illumination of said pattern, the at least three layers preferably representing a succession of at least three different positions of a similar body. The least three layers described herein may have a same color or may have different colors when viewed or observed under daylight.

According to one embodiment of the present invention, at least two of the at least three layers are adjacent to each other, or alternatively, the at least three layers are adjacent to each other. According to another embodiment of the present invention, at least two of the at least three layers are spaced apart, preferably by a distance less than 20 mm and more preferably by a distance less than 10 mm, or alternatively, the at least three layers are spaced apart, preferably by a distance less than 20 mm and more preferably by a distance less than 10 mm. According to another embodiment of the present invention, at least two of the at least three layers overlap each other (i.e. they are superimposed over each other), preferably partially overlap, or alternatively, the at least three layers overlap each other, preferably partially overlap. According to another embodiment of the present invention, the at least three layers are disposed on the substrate in a combined way, for example two of the at least three layers are adjacent to each other and the third one is spaced apart from the two adjacent layers; two of the at least three layers are adjacent to each other and the third one overlaps one or both of the two adjacent layers; or two of the at least three layers are spaced apart and the third one overlap each other one or both of the two spaced apart layers. When the layers are superimposed over each other (either partly or completely), it is necessary that each layer is visible under irradiation with the specific electromagnetic radiation with which the material comprised in said layer specifically interacts. The order of the superimposed layers can otherwise be freely chosen, e.g. the first layer containing the first material does not have to be the arranged below the second and third layers, but may also be arranged between or above the second and third layers.

The at least three layers do not need to have a specific shape. However, the combination of the at least three layers preferably represent a succession of at least three different positions of a similar body, i.e. the at least three layers represent successive steps of the visual motion of the body, said body being for example a motif, indicium, object, person or animal.

Figure 1E:
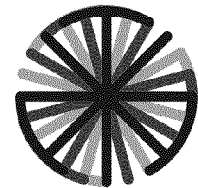

The present invention will now be further explained with the aid of non-limiting embodiments and drawings. In FIG. 1A, a side view of an embodiment of a security element of the present invention is shown. Sais security element comprises three layers 1 to 3 which are provided on a substrate S. FIGS. 1B to 1D schematically represent top views of said three layers 1 to 3 that when combined together and exposed to a sequential illumination form a visual motion of a body embodied as a wheel. FIGS. 1B to 1D represent a succession of three positions of said wheel and FIG. 1E represents a top view of the security element showing the combination of FIGS. 1B to 1D, i.e. a security element according to an embodiment of the present invention being formed by a superimposition of the three layers 1 to 3. FIG. 1E shows the combination of the three layers depicted in FIGS. 1B to 1D, wherein the axis of rotation of the wheel of each layer is superimposed over the axis of rotation of the wheel of two other layers, the spokes of the wheel are spaced apart and the partial representation of the circumference of the wheel partially overlap each others so that upon exposure to a sequential illumination, an impression of movement, i.e. a rotating wheel, is created in the eyes of an observer and serves as a highly efficient security element.

Figure 2A:
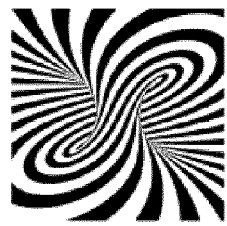
FIGS. 2A-2C represent another embodiment of the security element of the present invention which under sequential illumination exhibits a visual motion of a spiral.
Figure 2B:
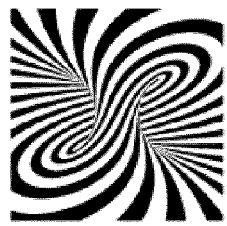
Figure 2C:
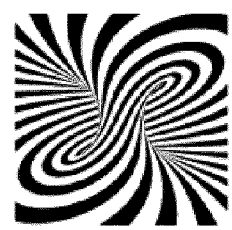

FIGS. 2A to 2C schematically represent another embodiment of the security element of the present invention comprising three superimposed layers that when combined together and exposed to a sequential illumination form a visual motion of a body embodied as a spiral. When combined together, the three squares of FIGS. 2A to 2C overlap each other so as to form a security element that, under exposure to a sequential illumination, forms a visual motion of a 3D moving spiral.

Figure 3A:
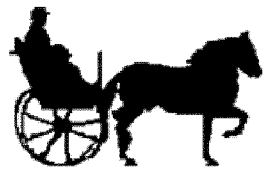
FIGS. 3A-3C represent another embodiment of the security element of the present invention which under sequential illumination exhibits a visual motion of a horse-drawn carriage.
Figure 3B:
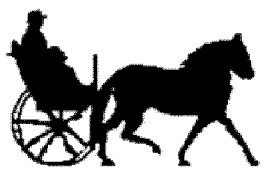
Figure 3C:
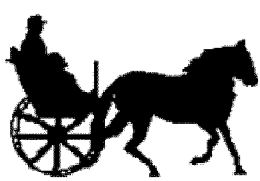

FIGS. 3A to 3C schematically represent another embodiment of the security element of the present invention comprising three superimposed layers that when combined together and exposed to a sequential illumination form a visual motion of a body embodied as a horse-drawn carriage. The combination of the three layers depicted in FIGS. 3A to 3C provides a security element according to an embodiment of the present invention, wherein some parts are superimposed (i.e. no movement will be visible for a viewer, see the head of the horse, the driver's body and the axis of rotation of the wheel for example) and some parts are spaced apart (see for example the spokes of the wheel) and some parts partially overlap each other (see the legs of the horse) so that upon exposure to a sequential illumination, an impression of movement, i.e. a rotating wheel and movement of the legs of the horse, is created in the eyes of an observer and serves as a highly efficient security element.

Figures 4A, 4B, 4C:
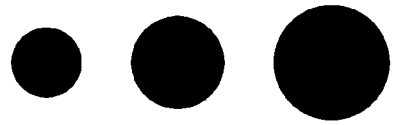
FIGS. 4A-4C represent another embodiment of the security element of the present invention which under sequential illumination exhibits a visual motion of a ball.

FIGS. 4A to 4C schematically represent another embodiment of the security element of the present invention comprising three layers that when combined together and exposed to a sequential illumination form a visual motion of a body embodied as a ball. All of the three layers depicted in FIGS. 4A to 4C are spaced apart with their center being aligned to each other according to a straight line. The combination of the three layers exhibit, upon exposure to a sequential illumination, an impression of movement, i.e. a rolling ball, is created in the eyes of an observer and serves as a highly efficient security element. Alternatively, the center of the three layers may be aligned to each other according to a parabola.

FIGS. 5A to 5C schematically represent another embodiment of the security element of the present invention comprising three layers that when combined together and exposed to a sequential illumination form a visual motion of a body embodied as a moon. All of the three layers depicted in FIGS. 5A to 5C are spaced apart with their center being aligned to each other according to a straight line. The combination of the three layers exhibit, upon exposure to a sequential illumination, an impression of movement, i.e. a waxing or waning moon, is created in the eyes of an observer. Alternatively, the center of the three layers may be aligned to each other according to a parabola.

FIGS. 5D to 5G schematically represent another embodiment of the security element of the present invention comprising three layers that when combined together and exposed to a sequential illumination form a visual motion of a body embodied as a moon. FIGS. 5D-5F are top views of superimposed layers of said security element providing different positions of said moon. FIG. 5G is a top view of said security element of showing the superimposition of the layers shown in FIGS. 5D-5F. The combination of the three layers exhibit, upon exposure to a sequential illumination, an impression of movement, i.e. a waxing or waning moon, is created in the eyes of an observer.

The security elements described herein are particularly suitable for the protection of a security document against fraud or illegal reproduction. Also described herein are uses of the security features described herein for the protection of a security document against fraud or illegal reproduction and security documents comprising the security element described herein. The term "security document" refers to a document having a value such as to render it potentially liable to attempts at counterfeiting or illegal reproduction and which is usually protected against counterfeit or fraud by at least one security feature. Examples of security documents include without limitation value documents and value commercial goods. Typical example of value documents include without limitation banknotes, deeds, tickets, checks, vouchers, fiscal stamps and tax labels, agreements and the like, identity documents such as passports, identity cards, visas, bank cards, credit cards, transactions cards, access documents, security badges, entrance tickets, transportation tickets, security threads and the like. The term "value commercial good" refers to packaging material, in particular for pharmaceutical, cosmetics, electronics or food industry that may comprise one or more security features in order to warrant the content of the packaging like for instance genuine drugs. Example of these packaging material include without limitation labels such as authentication brand labels, tax banderoles tamper evidence labels and seals.

Also described herein are processes for manufacturing security documents comprising the security element described herein as well as security documents obtained therefrom. The security documents described herein may be manufactured by a process comprising a step of applying onto a substrate, preferably by a coating or printing process, at least a first ink composition comprising said first material, preferably one or more left-handed circularly polarizing cholesteric liquid crystal materials, so as to form said first layer, applying, preferably by a coating or printing process, a second ink composition comprising said second material, preferably one or more right-handed circularly polarizing cholesteric liquid crystal materials, so as to form said second layer, and applying, preferably by a coating or printing process, a third ink composition comprising said third material, preferably, one or more luminescent materials, so as to form said third layer and so as to form a pattern providing a visual motion effect when exposed to a sequential illumination with a light source capable of separately emitting said first, second and third electromagnetic radiation, said pattern preferably comprising at least three layers representing a succession of at least three different positions of a similar body.

Preferably, the at least first, second and third ink compositions are applied by a coating or printing process. The first layer comprising said first material, preferably comprising the one or more left-handed circularly polarizing cholesteric liquid crystal materials described herein and the second layer comprising said second material, preferably comprising one or more right-handed circularly polarizing cholesteric liquid crystal materials described herein are preferably applied by a coating or printing process, and more preferably by a printing process independently selected from the group consisting of inkjet, screen printing, flexo printing and rotogravure and more preferably selected from the group consisting of screen printing, flexo printing and rotogravure. The third layer comprising said third material, preferably comprising the one or more luminescent materials described herein are preferably applied by a coating or printing process, and more preferably by a printing process selected from the group consisting of coating, inkjet, screen printing, flexo printing, rotogravure, intaglio (also known in the art as copperplate steel die printing) and offset. As known by those skilled in the art, inkjet may not be used to apply ink compositions comprising pigments and/or particles having a large particle size.

Screen printing (also referred in the art as silkscreen printing) is a stencil process whereby an ink is transferred to a surface through a stencil supported by a fine fabric mesh of silk, mono- or multi-filaments made of synthetic fibers such as for example polyamides or polyesters or metal threads stretched tightly on a frame made for example of wood or a metal (e.g. aluminum or stainless steel). Alternatively, the screen-printing mesh may be a chemically etched, a laser-etched, or a galvanically formed porous metal foil, e.g. a stainless steel foil. The pores of the mesh are block-up in the non-image areas and left open in the image area, the image carrier being called the screen. Screen printing might be flat-bed or rotary. Screen printing is further described for example in *The Printing ink manual*, R. H. Leach and R. J. Pierce, Springer Edition, $5^{th}$ Edition, pages 58-62 and in *Printing Technology*, J. M. Adams and P. A. Dolin, Delmar Thomson Learning, $5^{th}$ Edition, pages 293-328. For printing the first image, the second image and the third image of the security element described herein by a screen printing process, a stencil for each one of the images is produced by process known in the art, e.g. by producing stencil as described in e.g. Printing Technology, J M Adams and P. A. Dolin, Delmar Thomson Learning, 5th Edition, page 302-312:

Rotogravure is a printing process wherein the image elements are engraved into the surface of a cylinder. The non-image areas are at a constant original level. Prior to printing, the entire printing plate (non-printing and printing elements) is inked and flooded with ink. Ink is removed from the non-image by a wiper or a blade before printing, so that ink remains only in the cells. The image is transferred from the cells to the substrate by a pressure typically in the range of 2 to 4 bars and by the adhesive forces between the substrate and the ink. The term rotogravure does not encompass intaglio printing processes (also referred in the art as engraved steel die or copper plate printing processes) which rely for example on a different type of ink. More details are provided in "Handbook of print media", Helmut Kipphan, Springer Edition, page 48.

Flexography preferably uses a unit with a doctor blade, preferably a chambered doctor blade, an anilox roller and plate cylinder. The anilox roller advantageously has small cells whose volume and/or density determines the ink application rate. The doctor blade lies against the anilox roller, and scraps off surplus ink at the same time. The anilox roller transfers the ink to the plate cylinder which finally transfers the ink to the substrate. Specific design might be achieved using a designed photopolymer plate. Plate cylinders can be made from polymeric or elastomeric materials. Polymers are mainly used as photopolymer in plates and sometimes as a seamless coating on a sleeve. Photopolymer plates are made from light-sensitive polymers that are hardened by ultraviolet (UV) light. Photopolymer plates are cut to the required size and placed in an UV light exposure unit. One side of the plate is completely exposed to UV light to harden or cure the base of the plate. The plate is then turned over, a negative of the job is mounted over the uncured side and the plate is further exposed to UV light. This hardens the plate in the image areas. The plate is then processed to remove the unhardened photopolymer from the nonimage areas, which lowers the plate surface in these nonimage areas. After processing, the plate is dried and given a post-exposure dose of UV light to cure the whole plate. Preparation of plate cylinders for flexography is described in *Printing Technology*, J. M. Adams and P. A. Dolin, Delmar Thomson Learning, $5^{th}$ Edition, pages 359-360.

The ink compositions to be used in the present invention are conventional ink compositions for any of the above coating or printing processes. The at least first, second and third materials are incorporated into the ink compositions in such an amount that the desired visual motion effect can be satisfactorily observed. The amount of said materials varies with the desired effect and can be easily adjusted by a skilled man with his routine knowledge. When the ink compositions described herein comprise one or more cholesteric liquid crystal materials, in particular left-handed circularly polarizing cholesteric liquid crystal materials or right-handed circularly polarizing cholesteric liquid crystal materials, it is preferred that the one or more cholesteric liquid crystal materials are cholesteric liquid crystal pigments and that are present in an amount from about 5 to about 30 wt-%, the weight percent being based on the total weight of the ink composition.

When the ink compositions described herein comprise one or more luminescent materials, it is preferred that the one or more luminescent materials are present in an amount from about 0.1 to about 40 wt-%, the weight percent being based on the total weight of the ink composition.

The process for manufacturing the security element or security document described herein comprises a step of hardening the at least first, second and third ink compositions so as to form at least three layers. The at least first, second and third ink compositions described herein may be hardened as known to the skilled person by different methods. The hardening step generally may be any step that increases the viscosity of the ink composition such that a substantially solid material adhering to the substrate is formed. The hardening step may involve a physical process based on the evaporation of a volatile component, such as a solvent, and/or water evaporation (i.e. physical drying). Herein, hot air, infrared or a combination of hot air and infrared may be used. Alternatively, the hardening process may include a chemical reaction, such as a curing, polymerizing or cross-linking of the binder and optional initiator compounds and/or optional cross-linking compounds comprised in the ink composition. Such a chemical reaction may be initiated by heat or IR irradiation as outlined above for the physical hardening processes, but may preferably include the initiation of a chemical reaction by a radiation mechanism including without limitation radiation curing including Ultraviolet-Visible light radiation curing (hereafter referred as UV-Vis curing) and electronic beam radiation curing (E-beam curing); oxypolymerization (oxidative reticulation, typically induced by a joint action of oxygen and one or more catalysts, such as cobalt-containing, manganese-containing and vanadium-containing catalysts); cross-linking reactions or any combination thereof. Consequently, the at least first, second and third ink compositions described herein may be selected from the group consisting of radiation curable inks, thermal drying compositions, oxidatively drying intaglio inks and combinations thereof. Examples of suitable ink compositions may be found e.g. in The Printing Ink Manual, Ed R. H. Leach, R. J. Pierce, $5^{th}$ Edition.

The at least first, second and third ink compositions described herein may further comprise one or more machine readable materials. When present, the one or more machine readable materials are preferably selected from the group consisting of magnetic materials, electrically conductive materials, infrared-absorbing materials and mixtures thereof. As used herein, the term "machine readable material" refers to a material which exhibits at least one distinctive property which is detectable by a device or a machine and which can be comprised in a layer so as to confer a way to authenticate said layer or article comprising said layer by the use of a particular equipment for its detection and/or authentication.

The at least first, second and third ink compositions described herein may further comprise one or more additives including without limitation compounds and materials which are used for adjusting physical, rheological and chemical parameters of the composition such as the viscosity (e.g. solvents and surfactants), the consistency (e.g. fillers, extenders, anti-settling agents and plasticizers), the foaming properties (e.g. antifoaming agents), the lubricating properties (waxes), UV stability (photostabilizers) and adhesion properties, etc. Additives described herein may be present in one or more inks described herein in amounts and in forms known in the art, including in the form of so-called nano-materials where at least one of the dimensions of the additives is in the range of 1 to 1000 nm.

The at least first, second and third ink compositions described herein may be prepared by dispersing, mixing and/or milling all the ingredients forming liquid inks. When the at least first, second and third ink compositions described herein are UV-Vis-curable inks, the one or more photoinitiators may be added to the composition either during the dispersing or mixing step of all other ingredients or may be added at a later stage, i.e. after the formation of the liquid inks.

Suitable substrates for the present invention include without limitation paper or other fibrous materials such as cellulose, paper-containing materials, plastic or polymer substrates, composite materials, metals or metalized materials, glasses, ceramics and combinations thereof. Typical examples of plastic or polymer substrates are substrates made of polypropylene (PP), polyethylene (PE), polycarbonate (PC), polyvinyl chloride (PVC) and polyethylene terephthalate (PET). Typical examples of composite materials include without limitation multilayer structures or laminates of paper and at least one plastic or polymer material such as those described hereabove as well as plastic and/or polymer fibers incorporated in a paper-like or fibrous material such as those described hereabove. With the aim of further increasing the security level and the resistance against counterfeiting and illegal reproduction of security documents, the substrate may contain watermarks, security threads, fibers, planchettes, luminescent compounds, windows, foils, decals, coatings and combinations thereof.

The substrate described herein onto which the at least first, second and third ink compositions described herein are applied (in the case of superimposed layers only one layer is applied onto the substrate, the other layers being applied onto the previously applied layer), may consist in an intrinsic part of a security document, or alternatively, the at least first, second and third ink compositions described herein are applied onto an auxiliary substrate such as for example a security thread, security stripe, a foil, a decal or a label and subsequently transferred to a security document including without limitation value documents and value commercial goods in a separate step.

The security documents described herein may further comprise one or more additional layers or coatings either below or on top of the security element described herein, provided that the one or more additional layers do not interfere with the circular polarization of the first and second layers and provided that they do not interfere with the luminescence of the third layer. Should the adhesion between the substrate and the security element described herein be insufficient, for example, due to the substrate material, a surface unevenness or a surface inhomogeneity, an additional layer, coating or a primer between the substrate and the element might be applied as known for those skilled in the art.

As mentioned hereabove, colorshifting properties of cholesteric liquid crystal materials are easily observed when ink compositions comprising one or more cholesteric liquid crystal materials are applied directly or indirectly to an absorbing surface or to a background, preferably a sufficiently dark and even preferably a black surface or background. According to one embodiment of the present invention, the substrate of the security documents described herein has an absorbing surface to which the at least first, second and third layers are applied, and no further additional layer or coating is required to visually observe without any machine or device the colorshifting properties of cholesteric liquid crystal materials. According to another embodiment of the present invention, the substrate of the security documents described herein is not an absorbing layer and, therefore, the security document described herein further comprises an additional sufficiently dark and preferably a black background between the substrate and the ink composition. In the presence of a dark background, the dark background is applied to the substrate, prior to the application of the ink composition. Typical processes used to apply the dark background include without limitation inkjet, offset, screen printing, flexo printing and rotogravure.

With the aim of increasing the durability through soiling or chemical resistance and cleanliness and thus the circulation lifetime of security documents, one or more protective layers may be applied on top of element described herein, provided that the one or more protective layers do not interfere with the circular polarization of the first and second layers and provided that they do not interfere with the luminescence of the third layer. When present, the one or more protective layers are typically made of protective varnishes which may be transparent or slightly colored or tinted and may be more or less glossy. Protective varnishes may be radiation curable compositions, thermal drying compositions or any combination thereof. Preferably, the one or more protective layers are made of radiation curable, more preferably UV-Vis curable compositions.

Also described herein are methods for creating a visual motion during sequential illumination on a security element comprising the steps of:
i) providing the above described security element, and
ii) sequentially illuminating said security element with a light source capable of separately emitting at least said first, second and third electromagnetic radiation.

With the aim of creating an impression of visual motion of the security element described herein for an observer, the at least first, second and third layers of the security element described herein are exposed to a sequential illumination with an appropriate electromagnetic radiation at a frequency between about 2 Hz and about 10 Hz, preferably between about 2 Hz and about 8 Hz preferably between about 2 Hz and about 4 Hz. Each of the first, second and third layers is sequentially illuminated by a specific electromagnetic radiation which increases its contrast with respect to the other images.

The sequential illumination is performed by using an illuminating device comprising at least three light sources configured to produce electromagnetic radiation to illuminate at least a portion of the security element. When the security element comprises a first layer, a second layer and a third layer, the light source is configured to produce a first electromagnetic radiation, a second electromagnetic radiation and a third electromagnetic radiation. The light source can be configured to produce electromagnetic radiation that is at least one of the visible, ultraviolet or infrared wavelengths. Additionally the light source can be configured to produce electromagnetic radiation in a variety of configurations based on a number of lighting characteristics, including, for example, an amount of illumination (e.g. a specified number of light bulbs, an angle at which electromagnetic radiation is directed at the security element, a wavelength of the electromagnetic radiation, circularly polarization of the light waves or beams, or any combination of the foregoing. The light source can include any suitable type of electromagnetic radiation including, for example, a light emitting diode (LED), a laser diode (LD) an incandescent light, a fluorescent light, an ultraviolet light, an IR light or another suitable type of light. Each light can selectively be turned on to emit light or turned off. When the security element comprises a first layer, a second layer and a third layer, the light source comprises three sets of lights, preferably three sets of LED(s)

According to one embodiment of the present invention, when the security element comprises a) a first layer comprising one or more left-handed circularly polarizing cholesteric liquid crystal materials, b) a second layer comprising one or more right-handed circularly polarizing cholesteric liquid crystal materials and c) a third layer comprising one or more luminescent materials, the applying of a sequential illumination step (step ii)) is performed with the use of a light source comprising three sets of lamps, preferably three sets of LEDs, a first set of said sets being provided with a left polarizing filter, a second set of said sets being provided with a right polarizing filter and a third set of said sets being composed of a UV, Vis or IR lamp. As known for the person skilled in the art, the first and second layers of the security element under left-handed circular and right-handed circular polarization can be obtained in different ways, in each of them, however, the light source must have a left- and a right-circular polarizing filter, this can be done by: a) using two devices, one of them equipped with a left-handed and the other one equipped with a right-handed circular polarization filter, b) using a single device having beam-splitting and left- and right-handed polarization selection means, yielding a split image corresponding to the left- and the right-handed polarized view of the security element; or c) using a single device in combination with an electro-optic filter, such as disclosed in DE 102 11 310 A1, allowing for the alternative selection of right- and left-handed circular polarization.

Depending on the design of the pattern described herein as well as the visual motion to be created under sequential illumination, the order of the sequential illumination may be a constant sequence of the at least three electromagnetic radiations (i.e. electromagnetic radiation A, electromagnetic radiation B, electromagnetic radiation C, electromagnetic radiation A, electromagnetic radiation B, electromagnetic radiation C, etc.) or may be a non-constant sequence of the at least three electromagnetic radiations (i.e. electromagnetic radiation A, electromagnetic radiation B, electromagnetic radiation C, electromagnetic radiation B, electromagnetic radiation A, electromagnetic radiation C, etc.).

Also described herein are methods for authenticating a security document comprising the security element described herein, wherein the above method for creating a visual motion further comprises a step of authenticating said security element by verifying the visual motion effect.

In addition to the particularly high security level of the security element described herein provided by the dynamic visual motion when exposed to a sequential illumination, additional properties of the at least three layers described herein may be further used as authentication means to ascertain the genuineness of a security document comprising said security element. The security element made of the pattern comprising the at least three layers can be read by means of a device or a machine for a detectable parameter associated with each layer such as reflectance of the cholesteric liquid crystal materials of the first and second cholesteric liquid crystal layers and luminescence for the third layer. In particular, the at least three layers may exhibit a same or different reflectance (which is related to the position of a selective reflection band exhibited by the at least three layers). This information can be stored in a database, as a binary code for example, for later identification of the security element or security document comprising said security element based upon measurement of the detectable parameters using an appropriate reader. A search of the database can then be conducted to match the measured security element or security document comprising said security element to the stored code in the database.

EXAMPLES

The present invention is now described in greater detail with respect to non-limiting examples.

A security element comprising a first layer, a second layer and a third layer was prepared by screen printing a first ink composition (I1), a second ink composition (I2) and a third ink composition (I3) on a black coated paper, said three inks being UV-curable screen printing inks.

The ink compositions had the following formula:

| Ingredients | ink composition I1 wt-% | ink composition I2 wt-% | ink composition I3 wt-% |
|---|---|---|---|
| aliphatic polyester urethane acrylate | 27.9 | 27.9 | 27.9 |
| triacrylated reactive diluent | 25.0 | 25.0 | 25.0 |
| diacrylated reactive diluent | 20.0 | 20.0 | 20.0 |
| photoinitiator | 8.0 | 8.0 | 8.0 |
| antifoaming additive | 1.0 | 1.0 | 1.0 |
| fumed Silica | 0.5 | 0.5 | 0.5 |
| UV stabilizer | 0.5 | 0.5 | 0.5 |
| surfactant | 0.1 | 0.1 | 0.1 |
| left-handed circularly polarizing cholesteric liquid crystal pigments with a green to blue colorshift | 17.0 | — | — |
| right-handed circularly polarizing cholesteric liquid crystal pigments with a green to blue colorshift | — | 17.0 | — |
| green luminescent pigments | — | — | 17.0 |

The weight percent being based on the total weight of each ink composition.

100 g of each ink composition I1-I3 were prepared by mixing the ingredients described in Table 1. All ingredients except the surfactant and the pigments were mixed in a Dispermat® device with a 4 cm large propeller at 300-400 rpm for 1 minute and at 1500 rpm for 15 minutes. The pigments and the surfactant were added and the so-obtained mixture was mixed at 300-400 rpm for a period of 15 minutes. The temperature was controlled so as to not exceed 45° C. during the whole manufacturing process.

The ink composition I1 was manually applied to the substrate by a screen printing process (77-55Y silkscreens with a 10 cm wide blade) and was hardened under UV (two passes at 100 m/minutes under a Ga/In lamp and a Hg lamp at 15 A, each developing a 150 W/cm linear power) so as to form a first layer corresponding to FIG. 1A. The ink composition I2 was applied in register, i.e. the axis of rotation of the wheel being superimposed, the spokes of the wheel being spaced apart and the partial representation of the circumference of the wheel partially overlapping each other, by the same screen printing process described above to the substrate comprising the first layer and hardened as described above so as to form a second layer corresponding to FIG. 1B in register with the first image. The ink composition I3 was applied in register, i.e. the axis of rotation of the wheel being superimposed, the spokes of the wheel being spaced apart and the partial representation of the wheel circumference being partially overlapped, by the same screen printing process described above to the substrate comprising the first layer and the second layer and hardened as described above so as to form a third layer corresponding to FIG. 1C in register with the first image and the second image. The exact positioning of the three layers has been realized by the operator thanks to the transparency of the screens.

The so-obtained security element comprising the first, second and third layers corresponding to FIG. 1D was then exposed to a sequential illumination so as to create an impression of visual motion for an observer. The sequential illumination was performed with the use of a light source being a flashlamp comprising three sets of two LEDs, the first set (A) being composed of two white light LEDs (10000 mcd) surmounted with a left polarizing filter, the second set (B) being composed of two white light LEDs (10000 mcd) surmounted with a right polarizing filter and the third set (C) being composed of two 395 nm UV LEDs. The six LEDs were mounted and welded on the flashlamp so that their light beam was converging towards the same area of the security element, i.e. the central part of the printed security element. The sequential illumination was performed according to a constant sequence of the at least three sets of LED (i.e. A, B, C, A, B, C, etc.) at a frequency of 2.5 Hz.

The invention claimed is:

1. A security element comprising a pattern of at least three layers, wherein a first layer comprises a first material which is capable of interacting with a first electromagnetic radiation but does not interact with a second and third electromagnetic radiation, a second layer comprises a second material which is capable of interacting with said second electromagnetic radiation but does not interact with a first and third electromagnetic radiation, and a third layer comprising a third material which is capable of interacting with a third electromagnetic radiation but does not interact with a first and second electromagnetic radiation, wherein said pattern provides a visual motion effect when exposed to a sequential illumination with a light source capable of separately emitting at least said first, second and third electromagnetic radiation.

2. The security element according to claim 1, wherein the at least three layers represent a succession of different positions of a similar body.

3. The security element according to claim 1, wherein at least two of said layers are adjacent to each other, spaced apart from each other or at least partly superimposed over each other.

4. The security element according to claim 1, wherein said at least three layers have a same color or have different colors when viewed or observed under daylight.

5. The security element according to claim 1, wherein said first material is selected from the group consisting of one or more left-handed circularly polarizing cholesteric liquid crystal materials.

6. The security element according to claim 1, wherein second material is selected from the group consisting of one or more right-handed circularly polarizing cholesteric liquid crystal materials.

7. The security element according to claim 1, wherein said third material is selected from the group consisting of one or more luminescent materials.

8. The security element according to claim 1, wherein the first material is selected from the group consisting of one or more left-handed circularly polarizing cholesteric liquid crystal materials, the second material is selected from the group consisting of one or more right-handed circularly polarizing cholesteric liquid crystal materials and the third material is selected from the group consisting of one or more luminescent materials.

9. A process for manufacturing a security element recited in claim 1, comprising a step of applying, preferably by a coating or printing process, at least a first ink composition comprising said first material so as to form said first layer, and applying, preferably by a coating or printing process, at least a second ink composition comprising said second material so as to form said second layer, and applying, preferably by a coating or printing process, a third ink composition comprising said third material so as to form said third layer so as to form a pattern providing a visual motion effect when exposed to a sequential illumination with a light source capable of separately emitting said first, second and third electromagnetic radiation.

10. A use of the security element recited in claim 1 for the protection of a security document against fraud or illegal reproduction.

11. A security document comprising the security element recited in claim 1.

12. A method for creating a visual motion effect, comprising the steps of:
 i) providing a security element recited in claim 1;
 ii) sequentially illuminating said security element with a light source capable of separately emitting at least said first, second and third electromagnetic radiation.

13. The method according to claim 12, wherein the security element comprises a) a first layer comprising one or more left-handed circularly polarizing cholesteric liquid crystal materials, b) a second layer comprising one or more right-handed circularly polarizing cholesteric liquid crystal materials and c) a third layer comprising one or more luminescent materials and wherein the sequentially illuminating step is performed with the use of a light source comprising three sets of lamps, a first set of said sets of lamps being provided with a left polarizing filter, a second set of said sets of lamps being provided with a right polarizing filter and a third set of said sets of lamps being composed of a UV lamp.

14. The method according to claim 12, further comprising a step of authenticating said security element by verifying the visual motion effect.

15. The method according to claim 12, wherein said security element is provided on a security document.

* * * * *